US008100266B2

(12) United States Patent
Lackner et al.

(10) Patent No.: US 8,100,266 B2
(45) Date of Patent: Jan. 24, 2012

(54) LABORATORY STORAGE AND RETRIEVAL SYSTEM AND A METHOD TO HANDLE LABORATORY SAMPLE TUBES

(75) Inventors: Joachim Lackner, Mettmenstettem (CH); Ueli Stettler, Cham (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 236 days.

(21) Appl. No.: 12/460,819

(22) Filed: Jul. 23, 2009

(65) Prior Publication Data
US 2010/0028124 A1 Feb. 4, 2010

(30) Foreign Application Priority Data

Jul. 25, 2008 (EP) ..................................... 08013461

(51) Int. Cl.
*B07C 5/00* (2006.01)
(52) U.S. Cl. ............ 209/518; 209/552; 209/903; 422/65
(58) Field of Classification Search .................. 209/517, 209/518, 552, 903; 422/63, 65; 414/806
See application file for complete search history.

(56) References Cited

U.S. PATENT DOCUMENTS

| | | | | |
|---|---|---|---|---|
| 5,688,361 A * | 11/1997 | Itoh | ................................ | 156/362 |
| 5,721,384 A | 2/1998 | Tanihata | .................... | 73/864.81 |
| 5,985,215 A * | 11/1999 | Sakazume et al. | .............. | 422/67 |
| 6,068,437 A * | 5/2000 | Boje et al. | ................. | 414/331.02 |
| 6,220,451 B1 * | 4/2001 | Hoffmann | ..................... | 209/522 |
| 6,475,776 B1 * | 11/2002 | Higuchi | ...................... | 435/303.3 |
| 6,599,476 B1 | 7/2003 | Watson et al. | ................... | 422/63 |
| 6,926,058 B2 | 8/2005 | Sato et al. | ...................... | 156/556 |
| 7,214,023 B2 * | 5/2007 | Sato et al. | ...................... | 414/281 |
| 7,290,973 B2 * | 11/2007 | Sato et al. | ...................... | 414/281 |
| 7,314,341 B2 | 1/2008 | Malin | ....................... | 414/331.02 |
| 7,364,907 B2 * | 4/2008 | Weselak et al. | .................. | 436/43 |
| 7,545,972 B2 * | 6/2009 | Itoh | ................................ | 382/142 |
| 2002/0023444 A1 | 2/2002 | Felder et al. | .................... | 62/177 |
| 2003/0116480 A1 * | 6/2003 | Takizawa | ...................... | 209/583 |

(Continued)

FOREIGN PATENT DOCUMENTS
EP 0 467 302 1/1992

(Continued)

OTHER PUBLICATIONS
Office action in EP 08 013 461.2 dated Feb. 18, 2011.

(Continued)

*Primary Examiner* — Joseph C Rodriguez
(74) *Attorney, Agent, or Firm* — McDonnell Boehnen Hulbert & Berghoff LLP

(57) ABSTRACT

A laboratory storage and retrieval system and a method to handle laboratory sample tubes are disclosed. The laboratory storage and retrieval system for storing sample tubes and retrieving stored sample tubes comprises a rack handler section (12) and a storage section (14), the rack handler section (12) comprising a transport system and a determination unit, wherein the transport system receives and transports incoming primary racks (PR) containing sample tubes (S) to the determination unit for determining at least one given parameter of the sample tubes (S) relating to predetermined sort criteria in order to have the transport system unload the sample tubes from the analysed primary rack (PR) and resort the unloaded sample tubes into appropriate storage racks (SR) depending on the determined sample tubes' sort criteria parameter for storage in the storage section (14) in the storage racks.

14 Claims, 12 Drawing Sheets

U.S. PATENT DOCUMENTS

| | | | |
|---|---|---|---|
| 2003/0116481 A1* | 6/2003 | Takizawa | 209/583 |
| 2003/0116484 A1* | 6/2003 | Takizawa | 209/630 |
| 2004/0213651 A1 | 10/2004 | Malin | 414/331.05 |
| 2004/0267403 A1* | 12/2004 | Itoh | 700/214 |
| 2005/0053454 A1 | 3/2005 | Wiggli et al. | 414/752.1 |
| 2006/0177922 A1 | 8/2006 | Shamah et al. | 435/286.2 |
| 2007/0014469 A1 | 1/2007 | Paillet et al. | 382/159 |
| 2007/0172396 A1 | 7/2007 | Neeper et al. | 422/104 |
| 2008/0050278 A1* | 2/2008 | Farina et al. | 422/64 |
| 2010/0028203 A1* | 2/2010 | Frey et al. | 422/65 |
| 2010/0049358 A1* | 2/2010 | Koch et al. | 700/214 |

FOREIGN PATENT DOCUMENTS

| | | |
|---|---|---|
| EP | 1348965 | 10/2003 |
| EP | 1353183 | 10/2003 |
| EP | 1391401 | 2/2004 |
| EP | 1391402 | 2/2004 |
| EP | 2148206 A1 * | 1/2010 |
| FR | 2788042 | 7/2000 |
| JP | 09133687 | 5/1997 |
| WO | 1983/00393 | 2/1983 |
| WO | WO 99/28724 | 6/1999 |

OTHER PUBLICATIONS

Extended European Search Report in EP 08 01 3461, dated Dec. 19, 2008.

Handbook of Clinical Automation, Robotics and Optimization, G. Kost ed., Chapters 12 and 13, Wiley & Sons, Inc. (1996).

* cited by examiner

LABORATORY STORAGE AND RETRIEVAL SYSTEM AND A METHOD TO HANDLE LABORATORY SAMPLE TUBES

TECHNICAL FIELD

The present invention relates to the handling of sample tube racks in a laboratory environment, and particularly to a laboratory device for handling sample tubes in the context of storing such sample tubes in a storage compartment. More particularly, the present invention relates to an automated tubes storage resorting system.

DESCRIPTION OF THE RELATED ART

In laboratories, such as for example clinical laboratories in which patient samples are examined and submitted to various in-vitro diagnosis tests, test tubes containing samples (such as blood, urine, etc.) have to be handled in high number and in a cautious but still efficient manner. For years now, automated procedures with corresponding systems and devices have been used in this context.

One aspect during the handling of these sample tubes relates to the tubes being placed in a storage compartment, which can be, for example, a refrigerating device. For efficient handling purposes, the tubes are not handled individually but placed in so-called racks. Usually, the tubes are placed in the racks already by the client, i.e., the person, the department or the institution sending samples to the laboratory, and are then sent or transported to the laboratory in these racks. In the laboratory, the racks with the tubes are subject to further handling steps for testing. Very often, such racks contain tubes with different sizes, heights, diameters, contents, expiration dates of the samples etc., which complicates automated handling so that in some cases further automated insertion of the racks in the test process in the laboratory is not possible, the racks having to be discharged manually.

U.S. Pat. No. 7,314,341 discloses a storage system which has a cabinet with controlled climatic conditions, and ring-shaped holders to store the samples within its interior. An automatic transport system moves the samples, with a mechanism to load and unload them within the sample holders. The loading/unloading mechanism and/or the sample holders rotate around a centre axis. The samples are inserted and removed over the top of the assembly by a telescopic mechanism, with a vertical lift column and a transfer guide with a relative vertical movement at the lift trolley through a lock at the upper cover.

U.S. Pat. No. 5,985,215 discloses transferring of sample racks, in each of which a plurality of sample containers are held, from a rack feeding unit to a discrimination unit for discriminating a type of each sample container. After the discrimination unit, a plurality of analyzing units are installed along a transfer line, and pipetters of different types are provided in the respective analyzing units. The discrimination unit detects information on the length and the width of each sample container held in each sample rack by using an optical detector. A control part selects one of the analyzing units, suitable for analyzing the sample container of which type was discriminated, based on the information detected by the discrimination unit, and transfers the sample container of which type was discriminated, to a sample pipetting position in the selected analyzing unit.

Document WO 99/28724 A1 discloses a pathology distribution system for automated sample containers distribution. The system comprises a loading station for loading samples in primary containers of different types, a sample handling station for receiving the containers and identifying the container types and samples therein, and a container distribution station for distributing the containers in areas or racks in the distribution station marked for analysing processes prescribed for the samples therein. The handling station includes an image analyser for imaging the shape and colour of the cap on a container and/or other characteristic parts of the container for identifying the type of the container, and the sample in the container for determining the level and the volume of the sample available for aspiration if required. It also has a bar code reader for identifying the sample in the container.

SUMMARY

In one aspect a laboratory storage and retrieval system to store laboratory sample tubes and retrieve stored sample tubes is disclosed. The system includes a rack handler section and a storage section. The rack handler section comprising a transport system and a determination unit, wherein the transport system receives and transports incoming primary racks (PR) containing sample tubes (S) to the determination unit for determining at least one given parameter of the sample tubes (S) relating to predetermined sort criteria. The transport system unloads the sample tubes from the analysed primary rack (PR) and resorts the unloaded sample tubes into appropriate storage racks (SR) depending on the determined sample tubes' sort criteria parameter for storage of the storage racks in the storage section.

In another aspect, a method is disclosed for handling laboratory sample tubes in a laboratory storage and retrieval system. The laboratory storage and retrieval system includes a rack handler section and a refrigerating or storage section. The method comprises the steps of:
  in the rack handler section, transferring an incoming primary rack (PR) containing sample tubes (S) to a determination unit by means of a first robotic arm and determining at least one given parameter of the sample tubes (S) relating to predetermined sort criteria;
  unloading sample tubes (S) from the analysed primary rack (PR) by means of a second robotic arm and resorting the sample tubes (S) into storage racks (SR) depending on the determined sort criteria; and
  storing the storage racks (SR) in the storage section In operation, sample tubes contained in an incoming primary rack and which are to be stored in a storage device are retrieved from the primary rack, and each retrieved sample tube is inserted into a storage rack on the basis of given sort criteria.

Thus, sample tubes are not stored in the primary racks, which is cost effective as primary racks are more costly than storage racks. Further, the resorting of the sample tubes on the basis of given criteria allows a more effective use of the storage place available and a more effective handling of the tubes. For example, the resorting of the tubes can be done on the basis of geometric parameters of the tubes, such as tube diameter and/or tube height. This makes sure that tubes with a certain diameter or falling in a certain diameter range are placed in suitable storage racks with corresponding holding openings so that breaking of tubes because of a tube having a diameter too large for a given rack opening can be avoided. On the other hand, it is desirable that the diameter of the rack openings does not exceed the diameter of the sample tubes too much as this would result in a position of the tube in the rack with an unacceptably high inclination. Tubes which are inclined too much relative to the vertical are difficult to be handled by a robot. Preferably, the effective diameter of the rack openings is 10 to 30% larger than the diameter of the sample tubes to be stored therein.

Further, resorting can be done on the basis of the height of the sample tubes so that storage racks containing tubes within a given height range can be conveyed to certain areas in a storage device, e.g., shelves with a corresponding height distance to the next shelf, so that damaging of tubes due to them being too high for the storage location can be avoided. Further, resorting can be done on the basis of the content of the sample tubes which allows to group sample tubes according to given storage conditions, such as storage temperature. This avoids that samples are destroyed due to wrong storage conditions.

Still further, it is possible to resort the sample tubes on the basis of the expiration date (i.e., shelf life) of the content of the sample tubes which allows that all sample tubes contained in a storage rack can be discarded together once the shelf life has expired, which simplifies disposal of expired samples and avoids erroneous use of expired samples.

Further features and embodiments will become apparent from the description and the accompanying drawings.

It will be understood that the features mentioned above and those described hereinafter can be used not only in the combination specified but also in other combinations or on their own, without departing from the scope of the present disclosure.

Various implementations are schematically illustrated in the drawings by means of an embodiment by way of example and are hereinafter explained in detail with reference to the drawings. It is understood that the description is in no way limiting on the scope of the present disclosure and is merely an illustration of a preferred embodiment.

DETAILED DESCRIPTION

Reference will now be made in detail to some embodiments, examples of which are illustrated in the accompanying drawings. Wherever possible, the same reference numbers are used throughout the drawings to refer to the same or like parts.

Figure 1:
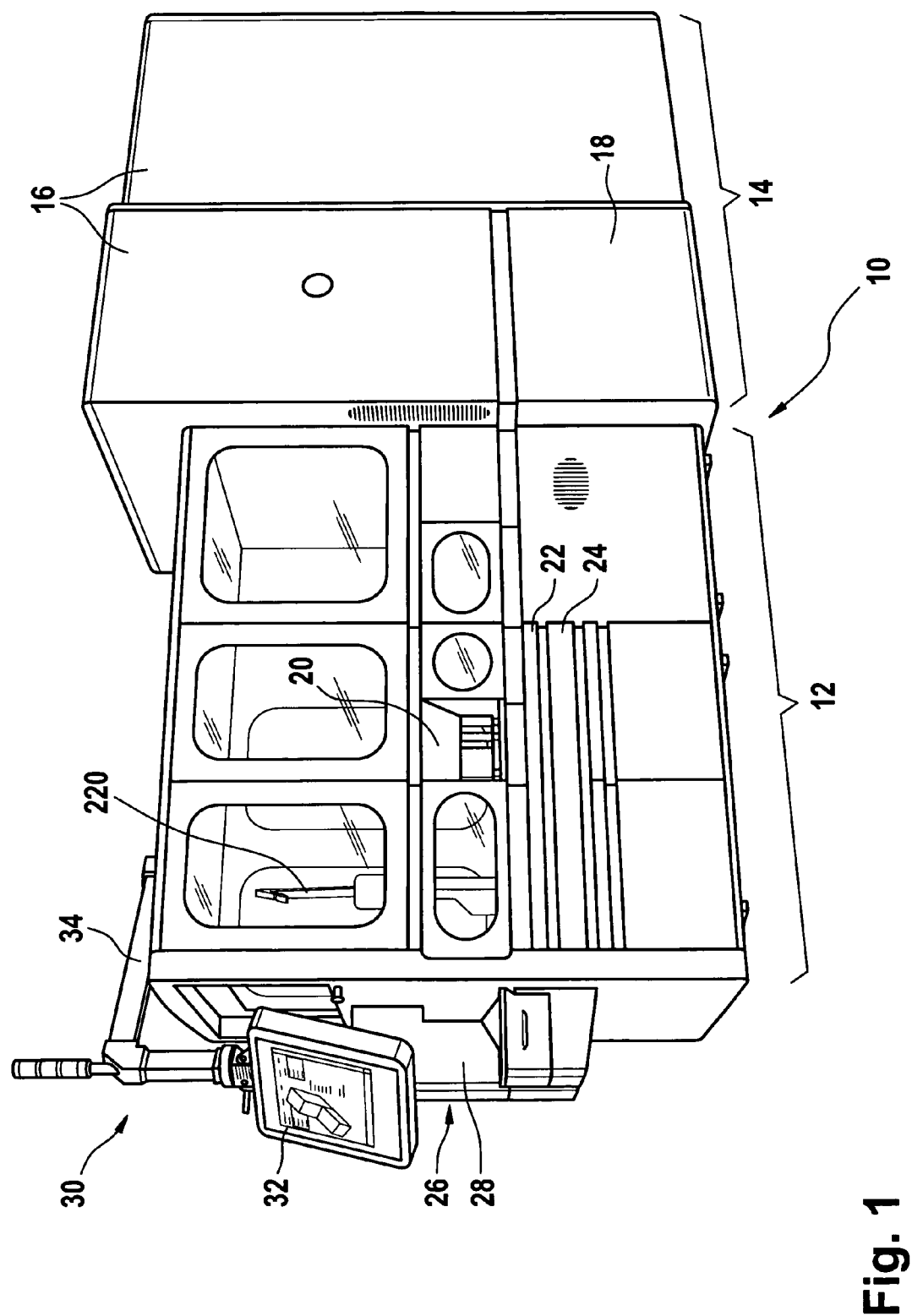
FIG. 1 shows a perspective view of a laboratory equipment unit comprising a laboratory system in which the invention can be practiced.

FIG. 1 shows a perspective view of a laboratory equipment unit 10 comprising a laboratory system in which the invention can be practiced. This laboratory equipment unit 10 may be a so-called storage retrieval module (SRM) forming part of an overall laboratory analyser system. The storage retrieval module comprises a rack handler section 12 (on the left hand side of the depiction of FIG. 1) and a storage (preferably a refrigerating or cooling) section 14 (on the right hand side of the depiction of FIG. 1). Between the two sections 12, 14, a loading/unloading interface (not shown) is provided through which racks are transferred from the rack handler section 12 into the refrigerating or cooling section 14 and back (in case of retrieval). This loading/unloading interface may include a gate or the like.

The storage section 14 may comprise a refrigerator 16. A storage section in the context of this invention is a cabinet of various size which is able to store a plurality of sample tubes in storage racks. The storage section may have a cooling unit to hold the ambient temperature for the tubes within the storage section below room temperature, possibly below 18° C. and possibly below 10° C.

The inside of the storage section 14 comprises a plurality of shelves for storage of a high number of sample tube racks. The sample tube racks loaded into the storage section are so-called storage racks, i.e. standardized racks. This implies that all tubes contained in primary racks (i.e. incoming racks of various types) fulfilling the geometry criteria of the invention are taken out of their respective primary racks and are re-sorted in suitable storage racks before being loaded into the storage section 14. The storage section may be large enough for one or two human beings being able to enter the inside of the storage section 14 through a door (not shown). In case the door is opened, a safety switching circuit ensures that all moving systems (like robotic arms or other transfer or conveying systems) come to a standstill, for example in a neutral or home position. While primary racks are single-row racks with somewhat standard geometry and therefore easy to handle in a plurality of different laboratory systems, the secondary racks and particularly the storage racks are multi-row racks (e.g. three rows with more than ten positions, for example 13 to 14 positions). Therefore, the secondary racks are more stable, particularly for storing purposes, and less likely to tilt over.

Further, the storage section 14 may comprise a disposal unit 18. The disposal unit 18 is connected with the storage section 14 via an internal opening (not shown) in a wall separating the storage section 14 from the disposal unit 18. Through this opening, sample tubes whose expiration date (i.e., shelf life) has elapsed can be disposed automatically in the disposal unit 18.

The rack handler section 12 has a housing consisting of several outer walls with windows so that operating personal can have a direct visual overview of the rack handler's functioning. The rack handler section 12 comprises an opening 20 in one of the outer walls through which primary racks can be inserted into the storage retrieval module 10. The opening 20 leads to the rack handler area 210 (cf., FIG. 2) which comprises at least one robotic arm 220 (which can be seen in the depiction of FIG. 1 through one of the windows). The opening 20 might be closable by means of a sliding or retractable door (not shown).

The rack handler section 12 further comprises drawers 22, 24 through which emptied primary racks and/or primary racks containing sample tubes with error designations and/or racks containing at least one retrieved sample tube can be taken out of the storage retrieval module 10.

Further, the rack handler section 12 comprises a capping station 26 with a feeder tank 28 for tube caps.

The storage retrieval module 10 also comprises a man-machine interface (MMI) 30 which might have the form of a touch screen monitor 32 at the end of an articulated arm 34.

Figure 2:
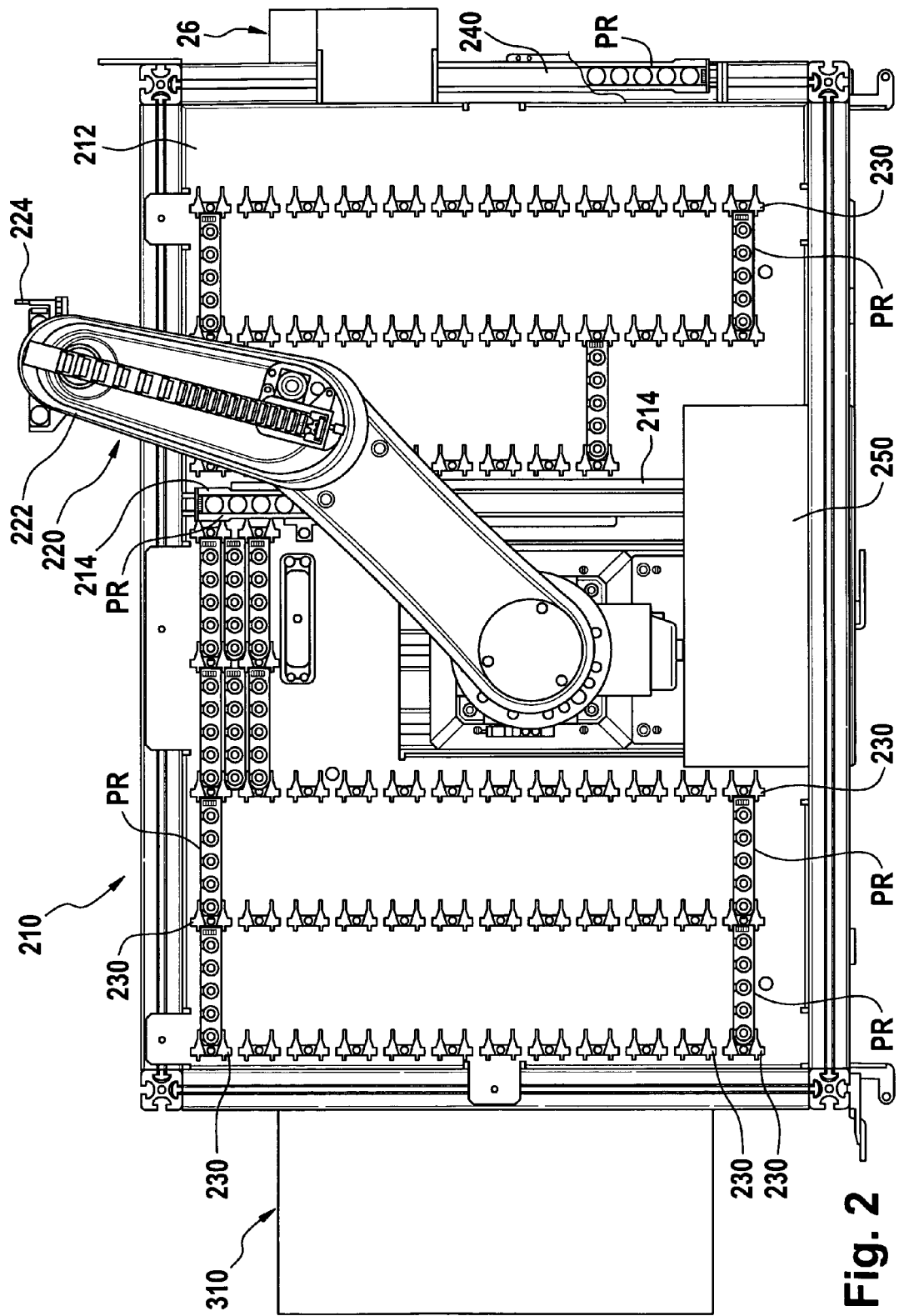
FIG. 2 shows a top view on a rack handler area of the laboratory system of FIG. 1 where incoming primary racks are handled.

FIG. 2 shows a top view of the rack handler area 210 of the storage retrieval module 10. The rack handler area 210 comprises a platform 212 inside the rack handler section 12 of FIG. 1. It further comprises a first robotic arm 220 which may be installed essentially in the centre of the platform 212 or at least at a position from which it can reach at least all locations within the rack handler area 210. Any known suitable robot can be used for this purpose. Preferably a SCARA robot with four axes and four degrees of freedom is employed. The robotic arm 220 comprises, at its end, a gripper 222 designed to securely grip the racks to be handled.

On the platform 212, a conveyor 214 is provided for conveying incoming primary racks PR containing sample tubes (e.g., five sample tubes) to an image analysing unit 250 which is also positioned on the platform 212.

Figure 15:
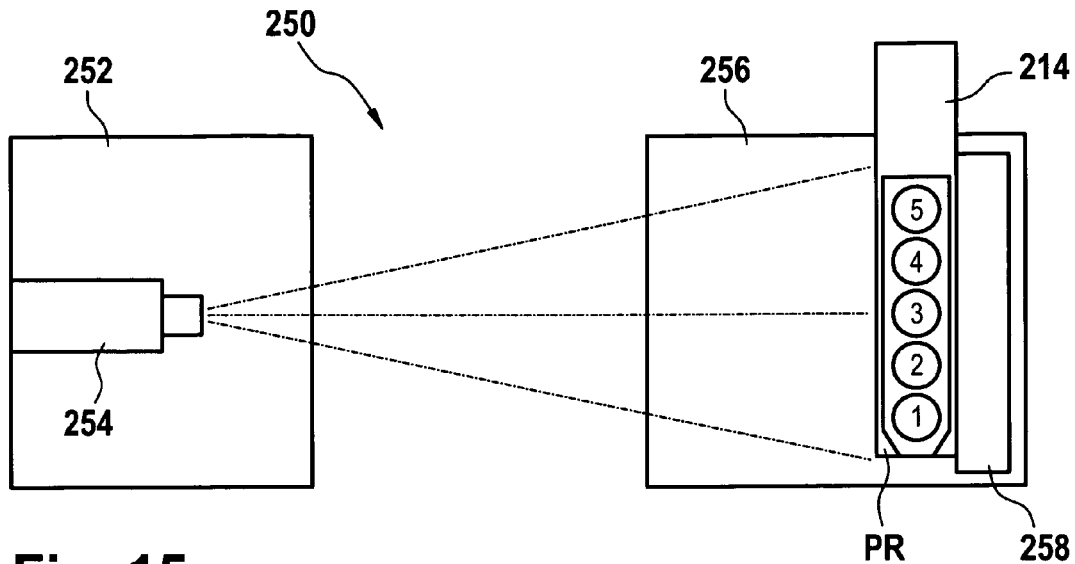
FIG. 15 shows a schematic top view of the image analysing unit of FIG. 2.

As shown in FIG. 15, the image analysing unit 250 comprises a first housing 252 in which a camera 254 is positioned, and a second housing 256 in which the conveyor 214 is leading in such a manner that a primary rack PR is conveyed into the second housing 256 into a predetermined position (examination position) in front of a backlight 258 providing homogenous lighting. The second housing 256 has the function of a light tunnel protecting the primary rack from extraneous light during image recording. The camera 254 is positioned so that it focuses on the predetermined rack position in front of backlight 258 and takes an image of at least all five sample tubes 1 through 5 in the primary rack PR, and also at least the upper portion of primary rack PR. In order to further improve homogeneity of the illumination, the background lighting may be provided with a ground-glass screen.

The image taken by the camera 254 is analysed as to various predetermined geometry parameters of the sample tubes 1 to 5 according to predetermined geometry criteria. The image analyser (which can be any suitable analyser of known type) can find and identify the various sample tubes 1 to 5 due to predetermined and known distances between the locations (23 mm in the shown example; only location 1 in the primary rack PR has a smaller width of 21.5 mm due to the shape of the primary rack which helps identify proper orientation of the rack).

One of the parameters to be analysed is the height of the sample tube above the upper edge of the primary rack PR. The total height of the sample tube including cap is defined as $h_{TC}$, and the height of the sample tube without cap is defined as $h_T$.

Another one of the parameters is the diameter of the sample tube which is defined as $d_T$. Still another parameter is the diameter of the cap which is defined as $d_C$. Presence of cap can be identified by determining whether $d_C > d_T$ and/or whether $h_{TC} > h_T$.

A further parameter is the angle of the sample tube in the rack, i.e. its inclination to the vertical which is the desired or optimum position. The angle can be determined by first determining the longitudinal axis of the tube by means of image analysing and then determining the angle between the longitudinal axis and the vertical. The angle of a sample tube in the rack is important to know as a sample tube which is too much inclined cannot be taken up by the gripper of the robotic arm properly and it might be broken by the gripper or might fall down and get smashed. Any breakages and smashes have to be avoided as this would result into a spilling of the contained fluid which is, very often, blood.

One further parameter is whether the barcode label which is applied to the outer surface (shell) of each tube is properly applied or sticking out (i.e., whether there is a spreading barcode label). This can be determined by checking if the diameter $d_T$ of a sample tube is constant all over its height $h_T$. Any deviation from a constant diameter might be an indication of a spreading barcode label. This is important to know as sample tubes with spreading barcode label are a hazard to handle, particularly when taking them out of the primary rack (where the sample tube might have got stuck due to the spreading barcode label) or when they are placed into another rack (which might not be possible because of the label material being in the way so that the tube cannot be inserted in the available opening of the target rack).

Figure 16:
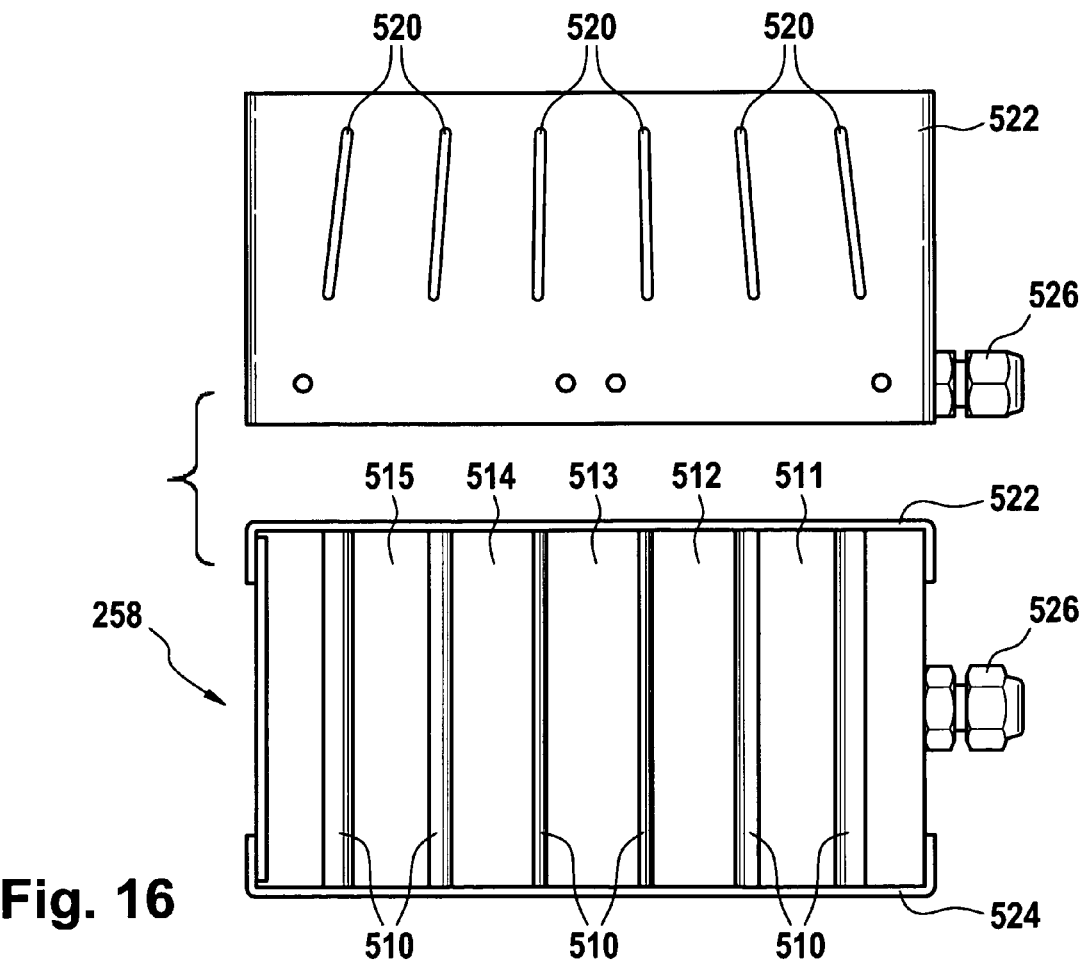
FIG. 16 shows a top and a front elevation of a backlight box of the image analysing unit of FIG. 15.

FIG. 16 shows a top (upper drawing) and a front (lower drawing) elevation of the backlight box 258 of the image analysing unit 250 of the invention. The backlight box 258 may consist in its simplest version of a box with five surrounding walls and an open front towards the camera 254. The interior of the walls may be designed in such a manner to promote homogenous lighting (originating from the backlight itself) and to prevent entrance of scattered light. As can be seen from the drawings of FIG. 16, the box may further contain fins or blades 510 extending substantially vertically through the interior of the backlight box and defining visual chambers 511, 512, 513, 514, 515 for the sample tubes 1, 2, 3, 4, 5 in a primary rack PR, correlating to the tube positions in the rack.

Apart from defining visual chambers, the fins 510 also reduce scattered light from one chamber to another so that picture or image quality is enhanced. The backlight box preferably emits monochrome light, possibly in a wavelength range of a few nanometres. The camera may record a grey value picture.

The fins 510 are positioned in slots 520 which are provided in a top wall 522 of the backlight box 258 (according slots may also be provided in the bottom wall 524 for better fixation of the fins). As can be seen, the fins 510 are not positioned in parallel to each other but with an angle adapted to the optical path of the lens of camera 254 in order to be aligned therewith. This means that on a picture or image taken by camera 254, each fin can be seen as a line delimiting a visual tube chamber from another, therefore facilitating the determination of presence of sample tubes in a given rack position and identification of the sample tubes.

On the right hand side in the drawings of FIG. 16, a port 524 for the electrical wiring for the backlight 258 is shown.

In operation, a primary rack PR is inserted into the second housing 256 within the image analysing unit 250 either in front of the fins 510 or behind the fins 510 (both options are basically possible; in the latter case, the primary rack is inserted between the backlight and the fins; the first option has the advantage that the fins reduce scattered light from one chamber to another, cf. above). Correct positioning is reached when each sample tube position of the primary rack is between two respective fins 510. An appropriate opening (not shown) is provided in one of the side walls of the second housing to allow insertion of the rack by means of conveyor 214 as already described above in reference to FIG. 15).

Further, a plurality of alignment elements 230 are provided on the platform 212. The alignment elements 230 are designed to hold in place the primary racks PR in a desired alignment or orientation which corresponds to an orientation of the gripper 222 of the robotic arm 220. In order to ensure proper orientation of the primary racks PR in every step of processing (such that sample tubes positions are always unambiguously identifiable), the primary racks may not be introduced directly on the conveyor 214 through the opening 20 but rather be taken up by the gripper 222 of robotic arm 220 and then placed on the conveyor 214. For this, a receiving position (not shown) for incoming racks is provided from which the robotic arm then takes up the incoming rack in order to place it onto the conveyor 214.

The conveyor 214 conveys the primary rack into the image analysing unit 250 where the sample tubes in the primary rack are analysed as to their geometry parameters. The determined geometry parameters of each sample tube are compared with predetermined geometry criteria and it is identified whether a sample tube is system conform or not. One of the geometry parameters to be analysed is the presence of a cap on the sample tube, and another geometry parameter to be analysed is the tube's diameter.

In case a sample tube is found to have no cap, the whole primary rack is sent to the capping station 26 before any other further processing of the primary rack or any of the other sample tubes contained therein. For this, the first robotic arm 220 places the primary rack onto a conveyor 240 conveying the primary rack with its sample tubes into the capping station 26 for a re-capping of the sample tube(s) identified to have no cap. After successful re-capping of the sample tube(s), the primary rack is brought back into the regular processing as explained in more detail below. Alternatively, as the case may be, the primary rack can be transferred back into the image analysing unit 250 in order to make sure that now all sample tubes carry a cap and are fit for further processing.

Figure 3:
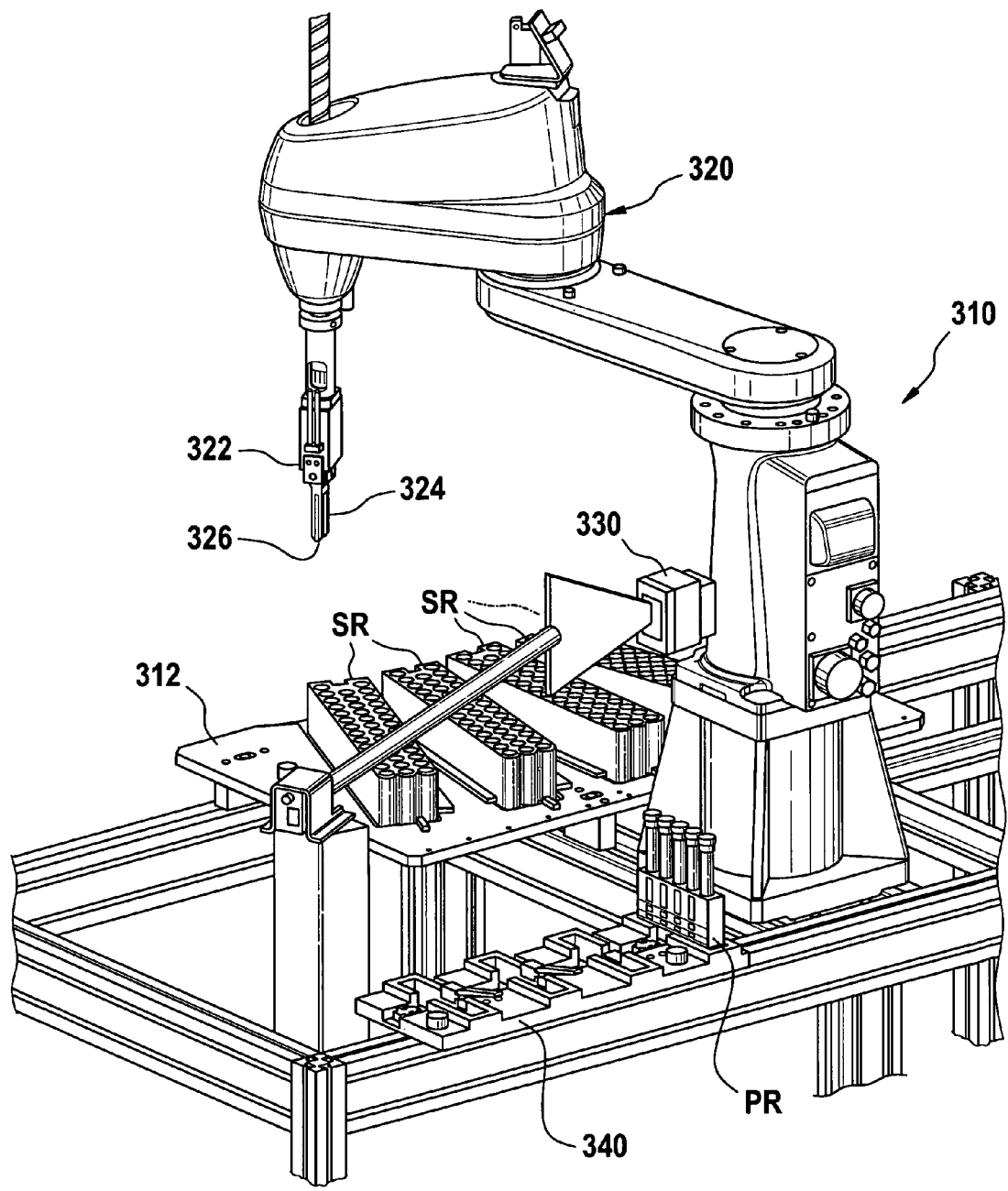
FIG. 3 shows a perspective rear view of a resorting station of FIG. 1.

FIG. 3 shows a perspective rear view of a resorting station 310. The resorting station 310 is also a part of the rack handler section 12 and is positioned adjacent to the rack handler area 210 of FIG. 2. For example, the resorting station 310 may be positioned on the left hand side of the rack handler area 210 in the depiction of FIG. 2, as indicated by reference numeral 310 in FIG. 2. As can be appreciated from the depiction of the drawings, the resorting station 310 is located outside of the storage section 14.

The resorting station 310 comprises a storage rack docking element 312 which is designed to receive a plurality of storage racks SR. The storage rack docking element 312 has basically the form of a substantially rectangular plate with a number of recesses 314 (five recesses in the embodiment shown in the drawings) adapted to fittingly receive according storage racks SR (cf., also FIG. 13), i.e., the recesses 314 act as holders for the storage racks. The resorting station 310 has at least two holders for holding storage racks, particularly for a first storage rack with openings of a first diameter and a second storage rack with openings of a second diameter.

The resorting station 310 further comprises a second robotic arm 320 which is positioned behind the storage rack docking element 312 in such a manner that a gripper 322 attached to the second robotic arm 320 may be able to reach any location within the resorting station 310. The second robotic arm 320 is of similar or identical type as the first robotic arm 220 of the rack handler area 210 as described above but is provided with a different gripper 322, namely a sample tube gripper whereas the first robotic arm 220 of the rack handler area 210 is provided with a primary rack gripper 222.

Figure 5:
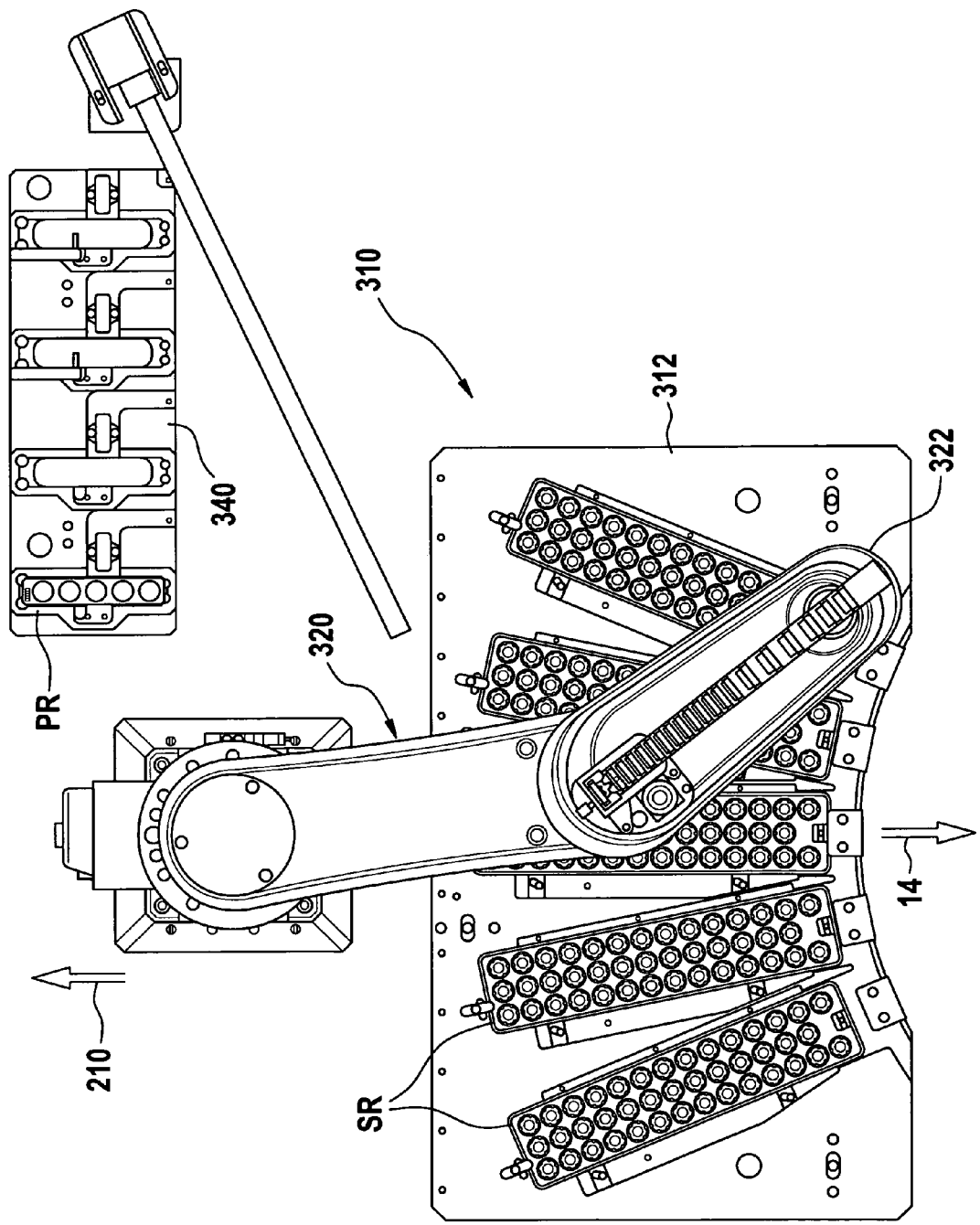
FIG. 5 shows a top view of the resorting station of FIG. 3.

Further, the resorting station 310 comprises a primary rack docking element 340 which is located at a position very close to the rack handler area 210 so as to be easily reachable by the first robotic arm 220 of the rack handler area 210 in order to be loaded with primary racks. In the top view illustration of FIG. 5, arrows with reference numerals 14 and 210, respectively, indicate the orientation of the resorting station 310, i.e. the primary rack docking element 340 and the back side of the second robotic arm 320 of the resorting station 310 are oriented towards the rack handler area 210 whereas the storage rack docking element 312 and the front side of the second robotic arm 320 are oriented towards the refrigerating or storage section 14.

In operation, a primary rack PR containing sample tubes S is conveyed into the image analysing unit 250 by means of conveyor 214 where the sample tubes S are analysed as to given predetermined geometric parameters in order to determine whether a sample tube is system conform or non-system conform. After this analysis, the primary rack PR is transferred, by means of the first robotic arm 220 of the rack handler area 210, to the primary rack docking element 340 (assuming that all sample tubes in the primary rack where found to carry a cap; otherwise there would first follow the re-capping procedure as described above, followed by another image analysis as the case may be).

Figure 6:
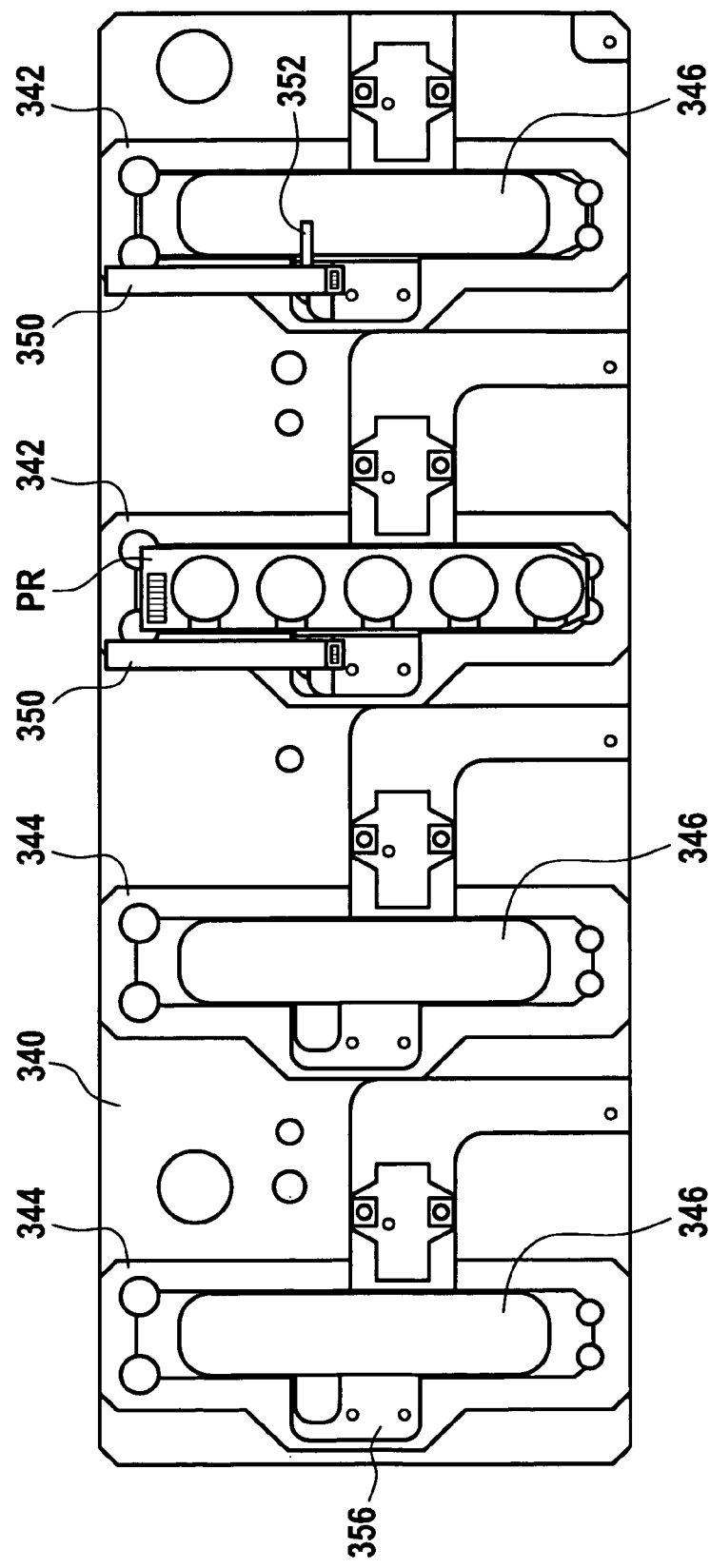
FIG. 6 shows an enlarged top view of a primary rack docking element of the resorting station of FIG. 3.
Figure 7:
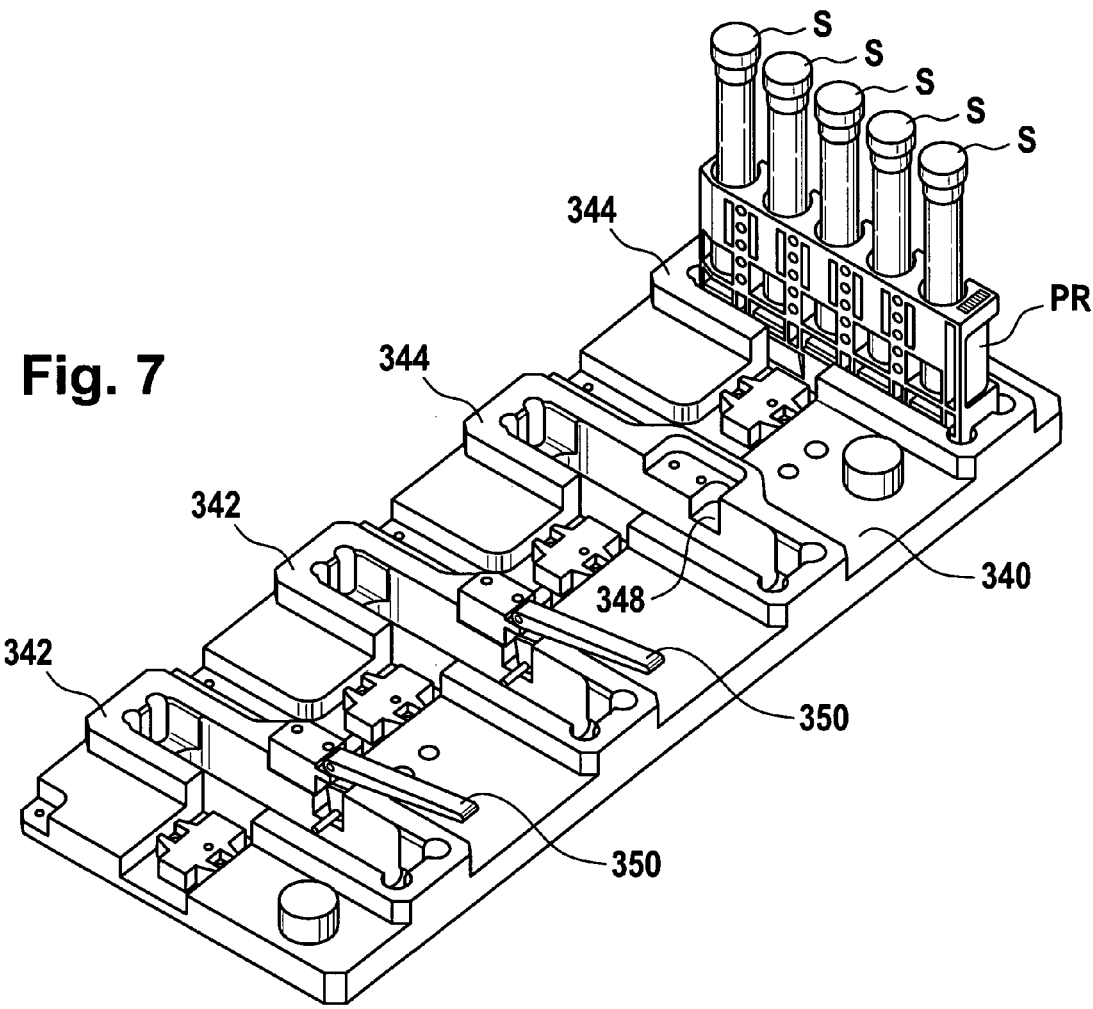
FIG. 7 shows a perspective view of the primary rack docking element of FIG. 6.
Figure 8:
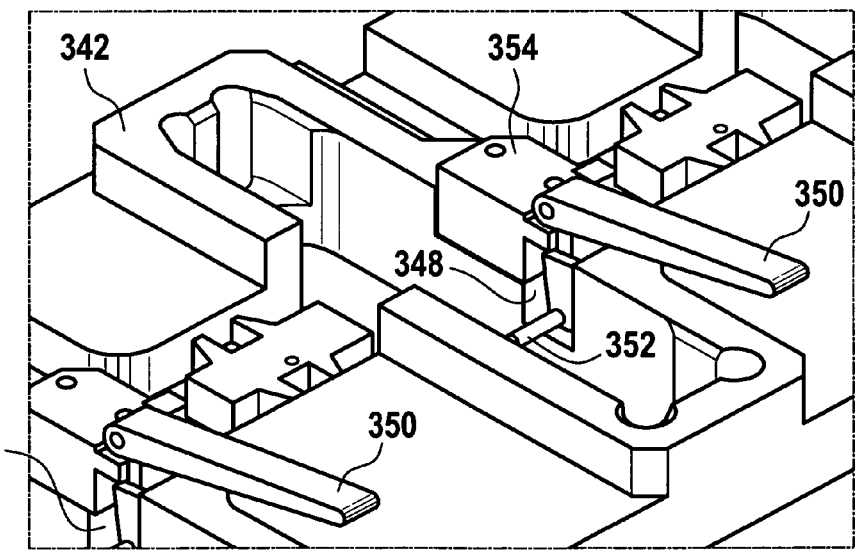
FIG. 8 shows an enlarged perspective view of a rack reception recess with a locking mechanism of the primary rack docking element of FIG. 6.

The primary rack PR is placed into a recess 346 of the primary rack docking element 340, adapted to fittingly receive a primary rack (cf. FIG. 6). As can be seen from FIGS. 6 to 8, the primary rack docking element 340 comprises four docking positions 442, 444, two of which (reference numeral 342) comprise a primary rack locking mechanism 350, 352, 354. The two docking positions 342 with a locking mechanism are destined to receive incoming primary racks, i.e. primary racks containing sample tubes to be unloaded and resorted into a storage rack SR. The two other docking positions 344 without a locking mechanism are destined to receive outgoing racks, i.e., racks to be loaded with sample tubes retrieved from the storage section.

The locking mechanism comprises a lever 350 which substantially has the form of an "L". The lever 350 is hingedly coupled to a base element 354 attached to primary rack docking element 340, the coupling being in such a manner that the longer "L"-leg of the lever 350 extends outside of the recess 346 and parallel thereto from about its centre to about its outer edge parallel to the longitudinal axis of the docking position. The shorter leg of L-formed lever 350 extends into a smaller opening 348 adjacent to the recess 346 and communicating therewith. The lever 350 is biased in relation to the base element 354 by means of a suitable biasing element, such as a helical spring or the like, so that it is upwardly inclined in its biasing position. Further, a pin 352 extends from the end of the shorter leg of lever 350 substantially perpendicular thereto, extending into the recess 346.

Figure 11:
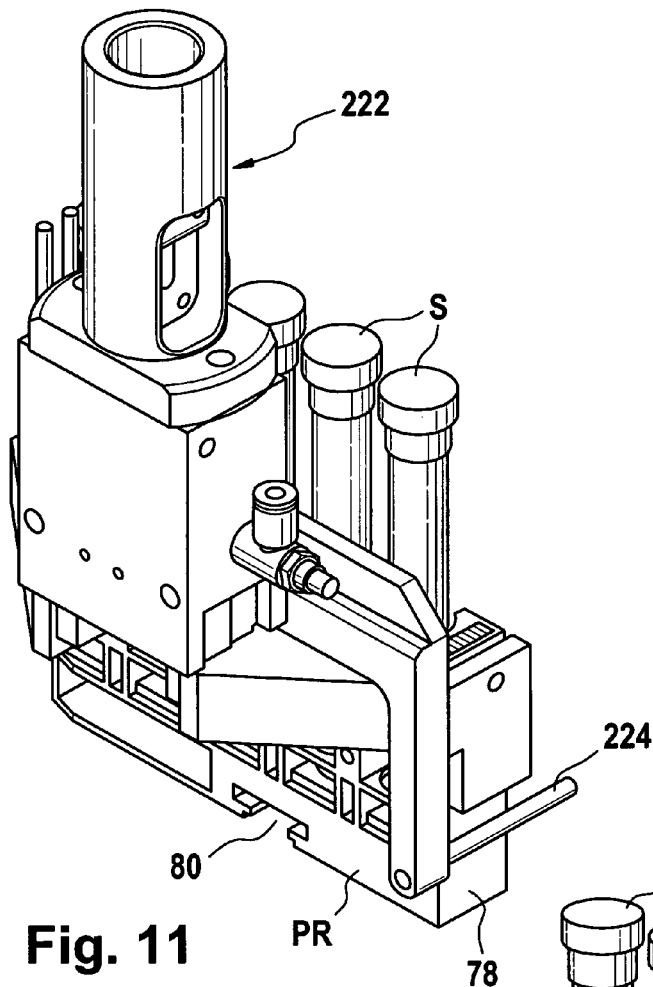
FIG. 11 shows a rear perspective view of a gripper of a robotic arm designed for interaction with the locking mechanism of FIG. 8.
Figure 12:
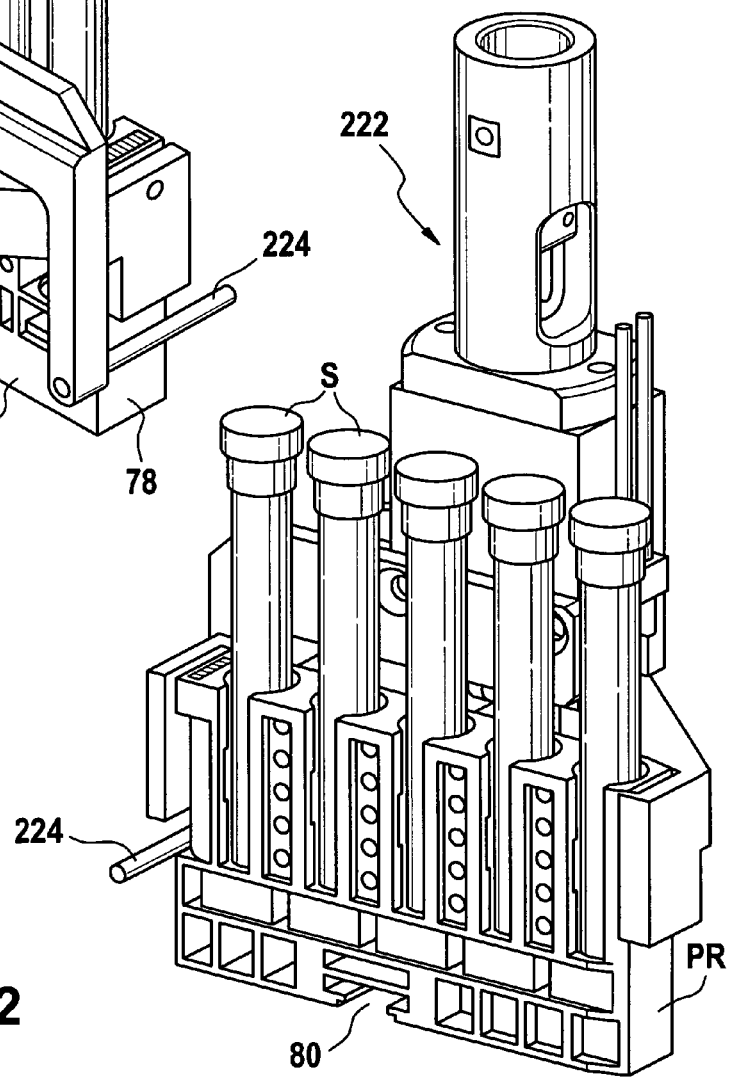
FIG. 12 shows a front perspective view of the gripper of FIG. 11.

The locking mechanism is actuated by a corresponding bolt 224 extending from the gripper 222 of the first robotic arm 220. The bolt 224 is attached to the gripper 222 in such a manner that it extends substantially horizontally below the gripper 222 and beyond the outer circumference of a primary rack PR when gripped by the gripper 222 at a front end 76 of the primary rack PR, i.e., the bolt 224 extends perpendicular to the longitudinal axis of the primary rack PR (cf., FIGS. 11 and 12).

Figure 9:
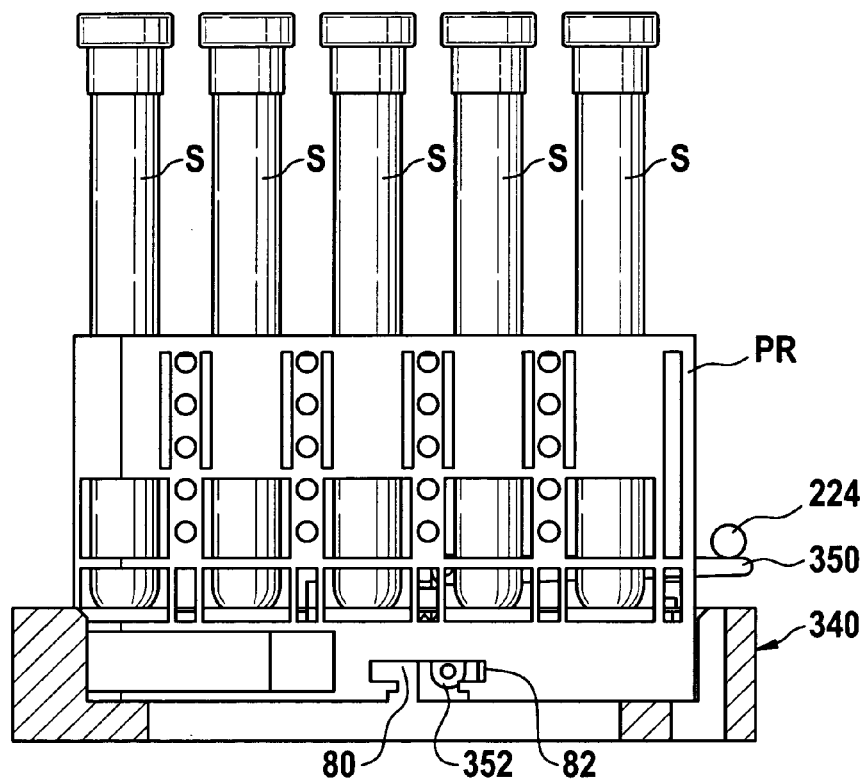
FIGS. 9 and 10 show a cross-section through the rack reception recess of FIG. 8, illustrating the operation of the locking mechanism.
Figure 10:
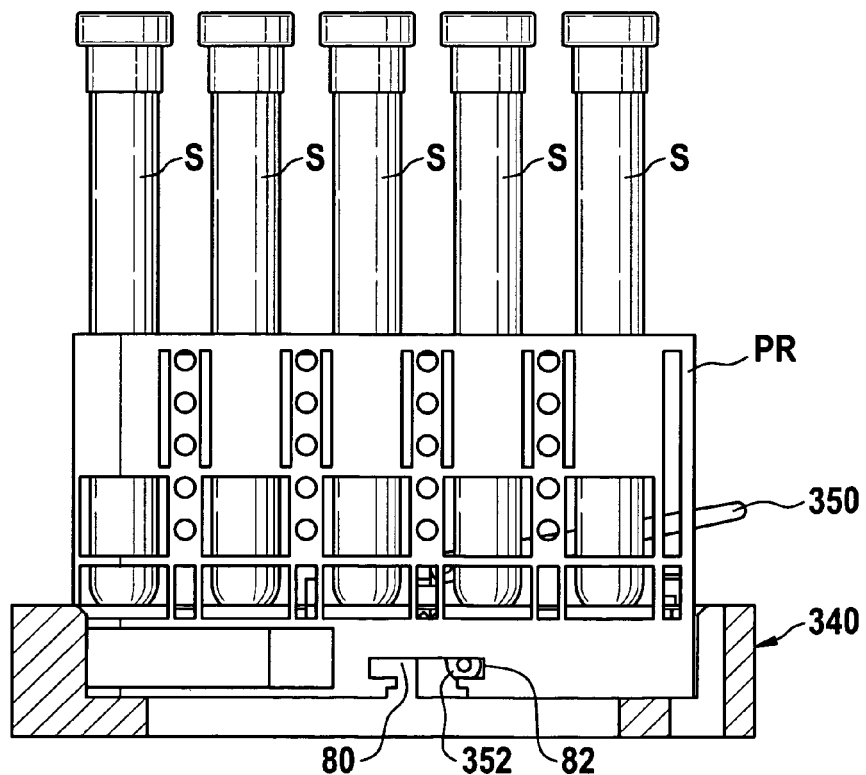

When the first robotic arm 220 places a primary rack PR into the primary rack docking element 340, it places the primary rack PR into the recess 346 of one of the receiving docking positions 342. When the first robotic arm 220 lowers the primary rack into the recess 346 of the receiving docking position 342, the bolt 224 contacts the outer end of the longer leg of lever 350 and forces it down against its biasing force such that the pin 352 swings into a receiving position in which it can engage a corresponding opening 80 in the bottom of primary rack PR (cf., FIG. 9).

When the gripper 222 releases the primary rack PR in the docking position 342 and moves back up, the bolt 224 also moves up and the lever 350 can swing back into it biasing position, thereby engaging with the pin 352 in an undercut slot 82 in the opening 80, thus locking the primary rack PR in the recess 346 in a stable position so as to allow unloading of the sample tubes S in a secure manner.

Figure 4:
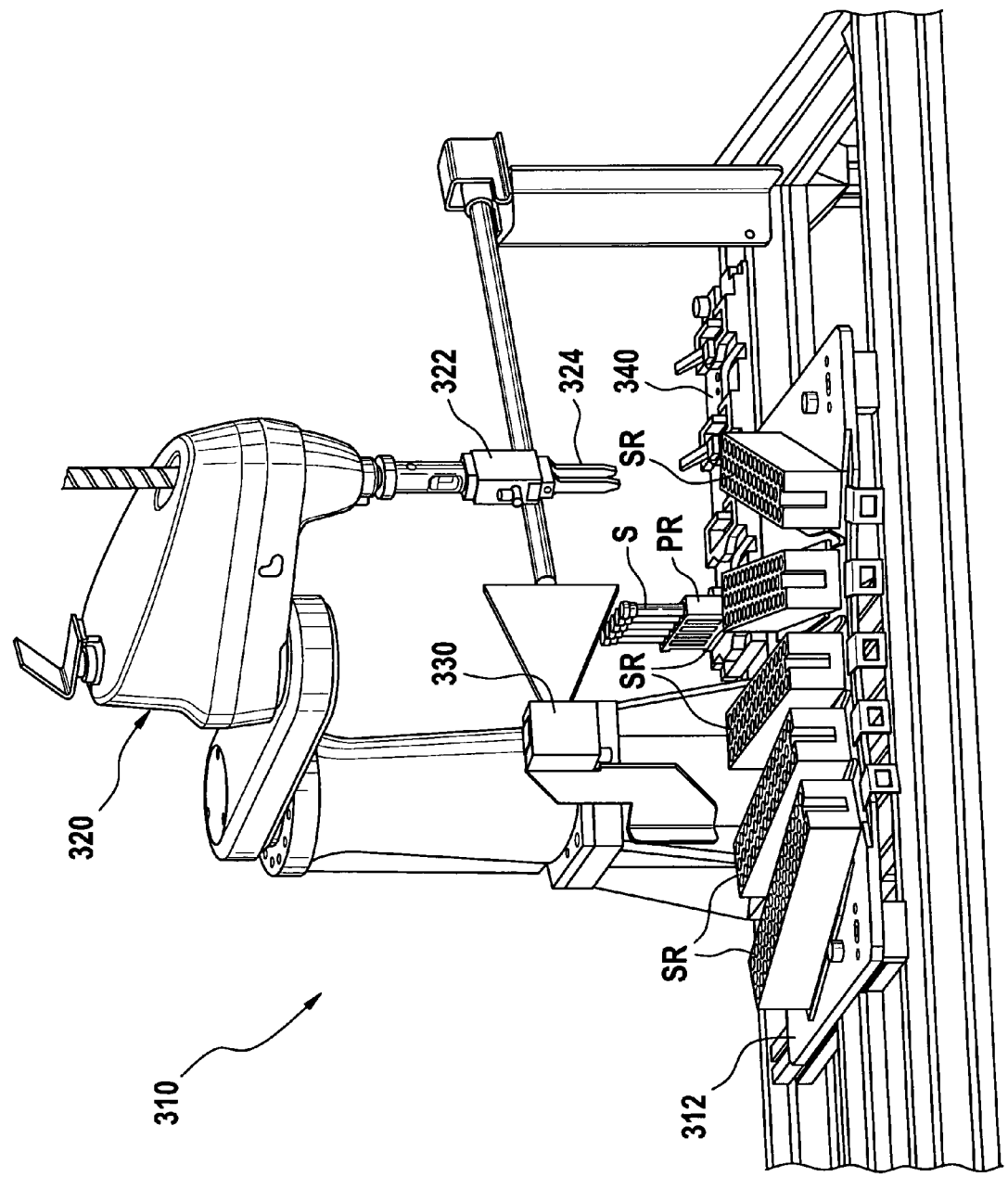
FIG. 4 shows a perspective front view of the resorting station of FIG. 3.

When a primary rack PR is positioned in the primary rack docking element 340 of the resorting station (cf., FIGS. 3 to 5), the second robotic arm 320 of the resorting station 310 starts unloading the sample tubes S contained in primary rack PR by taking them up subsequently with its tube gripper 322. The tube gripper 322 takes up a single sample tube S and moves it towards the storage rack docking element 312. On its way there, the sample tube S passes a barcode reader 330 which is positioned in front of the second robotic arm 320 in such a manner that the second robotic arm 320 may move the sample tube S, on its way to the storage racks SR, along the optical path of the barcode reader 330, at the same time rotating the sample tube so that the barcode applied to the outer surface of the sample tube can be read by the barcode reader 330. In order to enable barcode reading while the sample tube is being held by the sample tube gripper 322, the sample tube gripper 322 has a longitudinal slot 326 in each of its gripping fingers 324 as can be appreciated from the drawings of FIGS. 3 and 4.

As all electronic elements of the laboratory equipment unit 10, namely the robotic arms and their respective control units, the image analysing unit, the barcode readers etc., are connected to a central CPU with a database, the second robotic arm 320 "knows" which sample tube in the primary rack about to be unloaded is system conform and thus is to be unloaded. Therefore, only sample tubes which where categorized before as system conform will be unloaded in the resorting section 310 while the sample tubes which where categorized as non-system conform will remain in the primary rack.

In the resorting process, the control unit or CPU (not shown) controlling the resorting section resorts to data collected before during the image analysing process, i.e. the image identification result is stored in connection with a given sample tube, the sample tube being defined by the primary rack it is positioned in (to this end, every primary rack is provided with a barcode label for identification purposes) and its position within the primary rack (positions 1 to 5, cf., FIG. 15; orientation of the primary racks is unambiguously identifiable due to the asymmetric design of the primary racks) and used in the resorting section to "know" which sample tube is to be resorted in which storage rack.

By means of the barcode reader 330 of the resorting section 310, the system can retrieve additional data which may be relevant for correct resorting, such as for example sample tube's shelf life. In addition, if the according information is available from the barcode label, the system may double check the identity of the sample tube and/or if the sample tube held by the tube gripper 322 is system conform. It should be appreciated that all other suitable kind of information carrier can be used other than barcode labels. Particularly RFID tags (possibly in combination with barcode) are suitable as information and data collected in ones step (such as the image analysing step) can be written on the RFID tag and retrieved in any subsequent handling step (such as resorting or retrieving).

A plurality of storage racks SR is provided on the storage rack docking element 312 with various diameter openings for receiving sample tubes of various diameters from the second robotic arm 320. This means that all sample tubes with a given diameter are correspondingly put in an appropriate storage rack, and that only sample tubes with the same shelf life are put into the same storage rack. Other sorting criteria are, of course, possible, such as sample tube height. Thus, resorting may be based on more than one resorting criterion.

Figure 13:
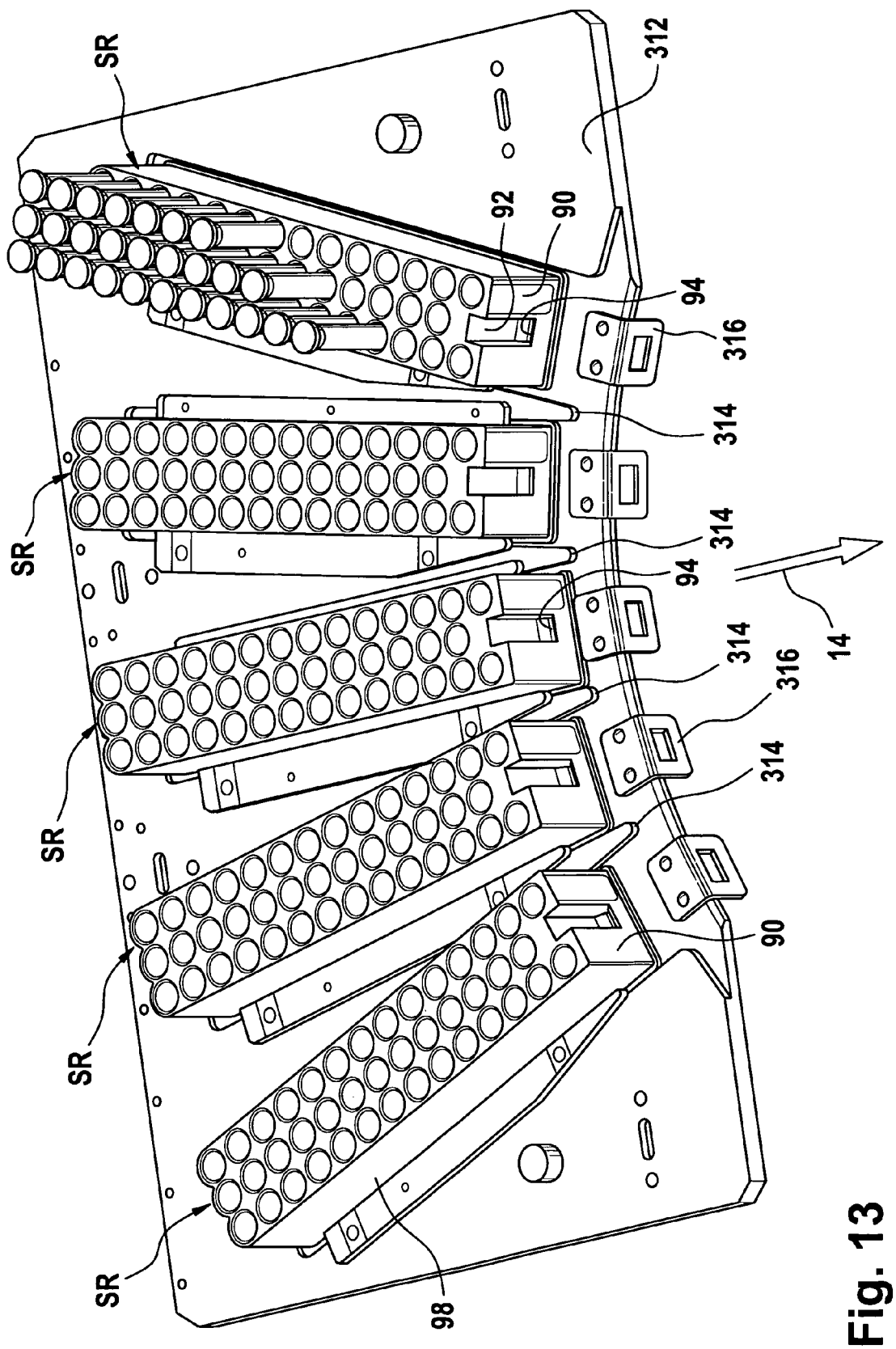
FIG. 13 shows a top perspective view of a storage rack docking element of the resorting station of FIG. 3.

As can be seen from FIG. 13, for example, the storage racks SR are not positioned in parallel to each other, but along a circle segment and pointing towards the gate (not shown) leading to the refrigerating or storage section 14 (i.e. the loading/unloading interface between the two sections 12, 14). When a storage rack is ready to be transferred into the refrigerator 16 of the storage section 14, the gate opens and a (third) robotic transfer system which is positioned within the refrigerator 16 extends trough the gate opening and takes up the according storage rack in order to transfer it into the refrigerator. A front surface 90 of each storage rack SR comprises a vertical slot 92, at the lower end of which a substantially horizontal circular opening 94 is provided. The third robotic transfer system may couple with the storage rack by engaging into the circular opening 94 with an appropriate complementary element, e.g. a hook with appropriate dimensions, and draw the storage rack onto a platform (not shown) of the third robotic transfer system.

The storage section may be pre-equipped at least partially with storage racks. The storage section may further have, in addition or alternatively to shelves, compartmented trays or inserts for the storage racks. Further, shelves or compartments with different heights are provided in order to be able to optimise available space when storing sample tubes of different heights. Another area may be reserved for error designated storage racks, e.g., racks containing non-identifiable tubes, defective tubes, tubes too high for proper handling, tubes with spreading barcode labels, mechanically defective racks, etc.) which may require manual handling.

Figure 14:
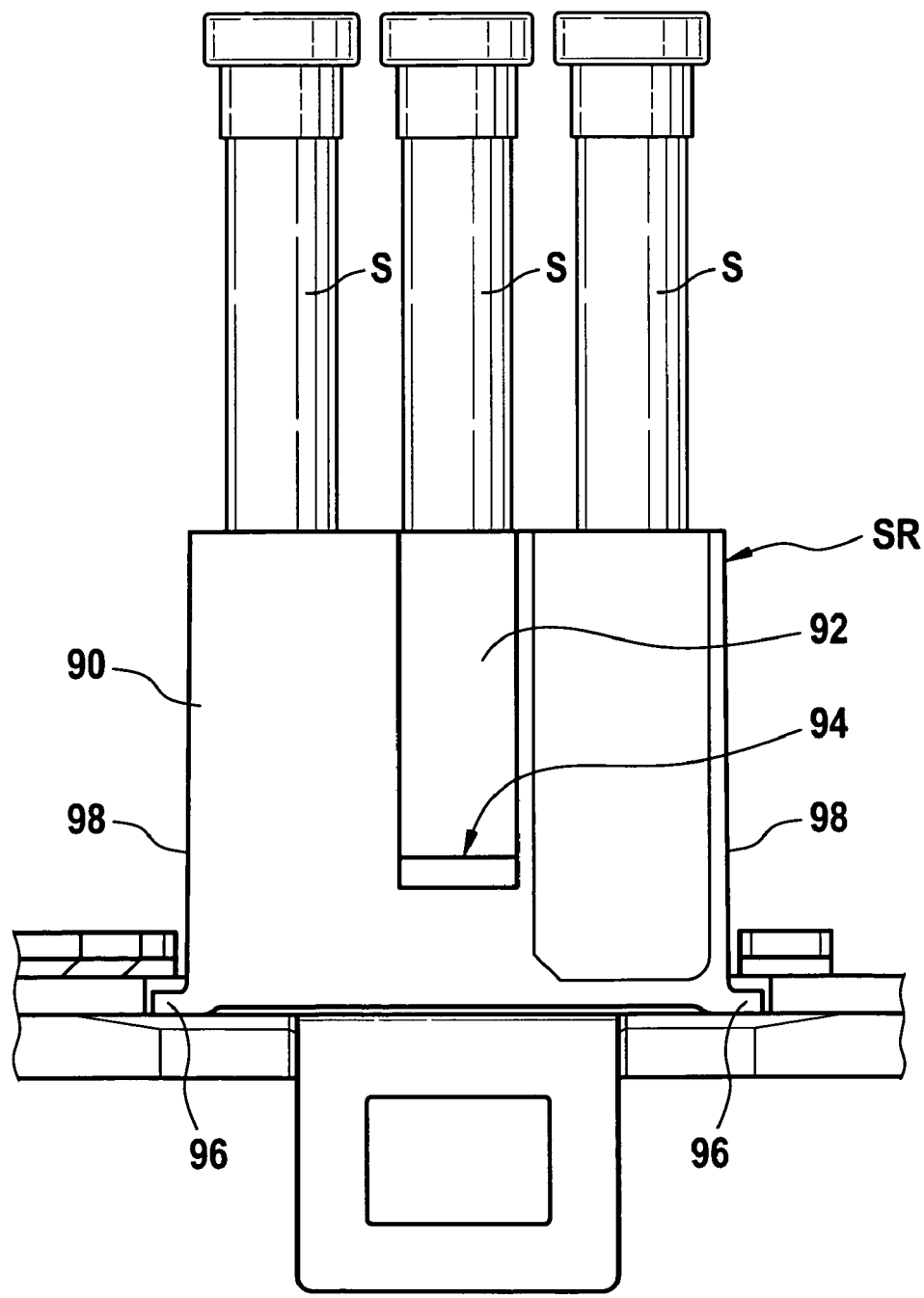
FIG. 14 shows an enlarged detail of the storage rack docking element of FIG. 13.

As can be seen from FIGS. 13 and 14, the storage rack docking element 312 is provided with a plurality of recesses for receiving the storage racks, the recesses having a T-slot cross-section in which the storage rack SR can slidingly engage with corresponding extensions 96 provided along the lower edges of its lateral faces 98.

If a sample tube is requested for additional tests or retesting, it is retrieved from the storage section according to the following procedure. First, the system (CPU) identifies the storage rack in which the requested sample tube is stored and then send controls signals to the third robotic transfer system to cause the third robotic transfer system to retrieve the according storage rack from the its shelf in the storage section 14 back through the loading/unloading interface to the resorting station 310 of the rack handler section 12 where the storage rack is placed into one of the recesses 314. The requested sample tube is then resorted from the storage rack SR into an outgoing primary rack by means of the second robotic arm 320. After this, the outgoing rack is transferred to an out-position (not shown), e.g. in a rack tray placed in a rack tray receiver assembly which might be located adjacent to the rack handler area 210, while the storage rack SR is transferred back into its shelf position in the storage section 14. The out-position can be the interface to an laboratory analyser (analytic module) and thus accessible to a robot arm of the analyser so that the rack can be directly further proceeded in an automated manner. Alternatively, the rack can be taken from the out-position manually. Furthermore, the cap on the requested sample tube may be automatically removed using the capping station 26 (FIG. 1) prior to placement of the outgoing rack in the out-position.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A laboratory storage and retrieval system to store sample tubes and retrieve stored sample tubes, comprising:
    a rack handler section (12) and
    a storage section (14),
    the rack handler section (12) comprising a transport system and a determination unit, wherein the transport system receives and transports incoming primary racks (PR) containing sample tubes (S) to the determination unit for determining at least one given parameter of the sample tubes (S) relating to predetermined sort criteria, the sort criteria comprising the sample tube (S) diameter;
    wherein the transport system unloads the sample tubes from the analysed primary racks (PR) and resorts the unloaded sample tubes into appropriate storage racks (SR) depending on the sample tubes' sort criteria for storage of the storage racks in the storage section (14); the storage racks (SR) comprising a first storage rack with openings of a first diameter to receive sample tubes (S) of a first diameter and a second storage rack with openings of a second diameter to receive sample tubes (S) of a second diameter.

2. The laboratory storage and retrieval system of claim 1, wherein the sort criteria further comprise a parameter selected from the group of parameters consisting of content of the sample tube, height of the sample tube, and shelf life of the sample tube.

3. The laboratory storage and retrieval system of claim 1, wherein the transport system comprises at least one first robotic arm (220) for handling incoming primary racks (PR) and at least one second robotic arm (320) for resorting sample tubes (S) from primary racks (PR) into storage racks (SR).

4. The laboratory storage and retrieval system of claim 1, wherein the storage section (14) comprises a storage transport system for transporting and handling the storage racks (SR), the storage transport system being designed to automatically retrieve a storage rack once the shelf lives of the sample tubes in the storage rack have expired and automatically disposes the sample tubes contained therein.

5. The laboratory storage and retrieval system of claim 1, further comprising a resorting station (310) which is located outside of the storage section (14), the resorting station (310) having at least two holders (314) for holding storage racks (SR).

6. The laboratory storage and retrieval system of claim 4, the storage section (14) further comprising a built-in disposal unit (18).

7. The laboratory storage and retrieval system of claim 3, further comprising a primary rack docking element (340) for accommodating primary racks (PR) to be unloaded or loaded by the second robotic arm (320), the primary rack docking element (340) comprising at least one recess (346) adapted to accommodate a primary rack (PR), which recess (346) is provided with a locking mechanism (350, 352, 354) for locking the primary rack (PR) in its docking position.

8. The laboratory storage and retrieval system of claim 7, wherein the locking mechanism (350, 352, 354) is actuated by a primary rack gripper (222) of the first robotic arm (220).

9. The laboratory storage and retrieval system of claim 1, further comprising a storage rack docking element (312) and wherein sample tubes to be retrieved from the storage section (14) are transferred in their storage rack (SR) to the storage rack docking element (312) where the sample tubes to be retrieved are resorted into outgoing primary racks.

10. A method for handling laboratory sample tubes in a laboratory storage and retrieval system for storing laboratory sample tubes and retrieving stored sample tubes, the laboratory storage and retrieval system comprising a rack handler section (12) and a refrigerating or storage section (14), the method comprising the steps of:
    in the rack handler section (12), transferring an incoming primary rack (PR) containing sample tubes (S) to a determination unit by means of a first robotic arm (220) and determining at least one given parameter of the sample tubes (S) relating to predetermined sort criteria, the sort criteria comprising the sample tube (S) diameter;
    unloading sample tubes (S) from the analysed primary rack (PR) by means of a second robotic arm (320) and resorting the sample tubes (S) into storage racks (SR) depending on the predetermined sort criteria, the storage racks (SR) being different from the primary racks (PR), and comprising a first storage rack with openings of a first diameter to receive sample tubes (S) of a first diameter and a second storage rack with openings of a second diameter to receive sample tubes (S) of a second diameter; and
    storing the storage racks (SR) in the refrigerating or storage section (14).

11. The method of claim 10, wherein the sort criteria further comprise a parameter selected from the group of parameters consisting of content of the sample tube, height of the sample tube and shelf life of the sample tube.

12. The method of claim 10, further comprising the step of determining with the determination unit whether a sample tube in the primary rack (PR) is non-system conform, and wherein any non-system conform sample tubes present in the primary rack are left in the primary rack (PR).

13. The method of claim 10, further comprising the steps of:
    removing a storage rack (SR) from the storage section (14);
    resorting a sample tube (S) for which sample an analytical test is desired from the removed storage rack into an outgoing primary rack; and
    transferring the outgoing primary rack to an out-position.

14. The method of claim 13, further comprising the step of automatically uncapping the sample tube (S) for which an analytical test is desired.

* * * * *